United States Patent
Prinz et al.

(10) Patent No.: US 7,420,076 B2
(45) Date of Patent: Sep. 2, 2008

(54) PROCESS FOR PREPARING DIALKYL DICARBONATES

(75) Inventors: Thomas Prinz, Leverkusen (DE); Markus Eckert, Hürth (DE); Hans-Ulrich Buschhaus, Krefeld (DE); Steffen Kahlert, Leichlingen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 11/596,026

(22) PCT Filed: Apr. 30, 2005

(86) PCT No.: PCT/EP2005/004724

§ 371 (c)(1),
(2), (4) Date: Nov. 8, 2006

(87) PCT Pub. No.: WO2005/110964

PCT Pub. Date: Nov. 24, 2005

(65) Prior Publication Data

US 2007/0213552 A1 Sep. 13, 2007

(30) Foreign Application Priority Data

May 13, 2004 (DE) .................. 10 2004 023 607

(51) Int. Cl.
*C07C 69/96* (2006.01)
*C07C 51/56* (2006.01)

(52) U.S. Cl. .................. 558/264; 562/894; 558/276

(58) Field of Classification Search .................. 558/264
See application file for complete search history.

(56) References Cited

U.S. PATENT DOCUMENTS

| | | | | |
|---|---|---|---|---|
| 3,128,297 A * | 4/1964 | Kanner et al. | ............... | 556/465 |
| 3,179,714 A * | 4/1965 | Brockman et al. | .......... | 525/535 |
| 3,206,519 A * | 9/1965 | Eberhardt | .................... | 585/457 |
| 3,220,975 A * | 11/1965 | Fox | ............................ | 528/199 |
| 3,240,796 A * | 3/1966 | Thoma et al. | ............... | 558/276 |
| 3,326,958 A * | 6/1967 | Curtius et al. | ............... | 558/260 |
| 4,929,748 A * | 5/1990 | Franklin | ..................... | 558/276 |
| 5,231,211 A * | 7/1993 | Tang | .......................... | 558/276 |
| 5,523,481 A * | 6/1996 | Pies et al. | .................... | 562/894 |
| 6,221,534 B1 * | 4/2001 | Takeuchi et al. | ............ | 429/347 |

FOREIGN PATENT DOCUMENTS

FR 1483560 6/1967

* cited by examiner

*Primary Examiner*—Yvonne Eyler
*Assistant Examiner*—Louisa Lao
(74) *Attorney, Agent, or Firm*—Nicanor A. Kohnoke

(57) ABSTRACT

The novel process for preparing dialkyl dicarbonates by reacting the corresponding alkyl haloformates with alkali metal hydroxides, alkaline earth metal hydroxides and/or carbonates in the presence of water-immiscible organic solvents and in the presence of a catalyst is characterized in that the catalyst used is at least one tertiary alkylamine of the formula (I)

$$NR^1R^2R^3,\qquad (I)$$

where the substituents are each as defined in the description.

12 Claims, No Drawings

PROCESS FOR PREPARING DIALKYL DICARBONATES

The present invention relates to a novel process for preparing dialkyl dicarbonates from the corresponding alkyl chloroformates using specific tertiary alkylamines as catalysts.

Dialkyl dicarbonates find use, for example, as catalysts for the oxidation of sterically demanding amines, as constituents of electrolyte fluids or as constituents of antimicrobial reagents. Dialkyl dicarbonates are also described in the literature as dialkyl pyrocarbonates.

DE-B 1 210 853 (1961) discloses the reaction of carbonic halides or carbonyl halides with organic hydroxyl compounds or the alkali metal or alkaline earth metal salts thereof and organic water-immiscible solvents and at least equivalent amounts of alkali metal or alkaline earth metal hydroxides or carbonates in a biphasic system, also using catalytic amounts of tertiary amines or quaternization products thereof, the amines or quaternization products thereof used being those which bear at least one ω-hydroxyalkyl, ω-hydroxyalkyl ether or ω-hydroxyalkyl polyether group bonded to nitrogen.

DE-A 1 418 849 (1961) also describes tertiary amines as particularly suitable catalysts for the preparation of acid derivatives whose tertiary nitrogen atoms are not sterically hindered, excluding tertiary amines, which bear as substituents on the nitrogen the same ω-hydroxyalkyl, ω-hydroxyalkyl ether or ω-hydroxyalkyl polyether groups. In addition to triethylamine and tri-n-butylamine, amines are therefore used here which bear at least one methyl group on the nitrogen, for example N-methyl-di-n-stearylamine. However, these catalysts have disadvantages including their catalysis not only of the formation but also the decomposition of the product, which leads to a reduction in the yield.

There is therefore a need for an improved preparation process which affords the target product in high yield.

It has been found that, surprisingly, dialkyl dicarbonates can be obtained particularly advantageously from alkyl haloformates by reaction with alkali metal or alkaline earth metal hydroxides or carbonates when the catalysts used are specific long-chain tertiary alkylamines.

These are notable for a high catalytic activity without having a decomposing action on the end product, and can be readily removed from the product, for example by distillation.

The present invention accordingly provides a process for preparing dialkyl dicarbonates by reacting the corresponding alkyl haloformates with alkali metal hydroxides, alkaline earth metal hydroxides and/or carbonates in the presence of water-immiscible organic solvents and in the presence of a catalyst, characterized in that the catalyst used is at least one tertiary alkylamine of the formula (I)

$$NR^1R^2R^3 \quad (I)$$

where $R^1$, $R^2$ and $R^3$ are each independently straight-chain or branched $C_6$-$C_{25}$-alkyl or $C_5$-$C_8$-cycloalkyl.

When the process according to the invention is carried out, the catalysts used are preferably tertiary alkylamines of the formula (I) where $R^1$, $R^2$ and $R^3$ are each independently straight-chain or branched $C_8$-$C_{16}$-alkyl or $C_6$-cycloalkyl.

When the process according to the invention is carried out, particularly preferred catalysts are trisoctylamine, trisisooctylamine, trislaurylamine, triscaprylylamine or any mixtures of these amines.

The process according to the invention preferably serves to prepare dialkyl dicarbonates of the formula (II)

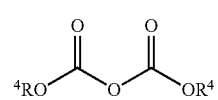

where
$R^4$ is straight-chain or branched $C_1$-$C_{20}$-alkyl by reacting alkyl haloformates of the formula (III)

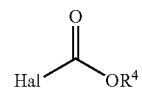

where
Hal is halogen, preferably F, Cl, Br, I, in particular chlorine, and
$R^4$ is straight-chain or branched $C_1$-$C_{20}$-alkyl, characterized in that the reaction is carried out in the presence of at least one tertiary alkylamine of the formula (I)

$$NR^1R^2R^3$$

where
$R^1$, $R^2$ and $R^3$ are each independently straight-chain or branched $C_6$-$C_{25}$-alkyl or $C_5$-$C_8$-cycloalkyl, preferably straight-chain or branched $C_8$-$C_{16}$-alkyl or $C_6$-cycloalkyl, as a catalyst.

In the formulae (II) and (III), $R^4$ is preferably straight-chain or branched $C_1$-$C_8$-alkyl, more preferably a —CH—$R^5R^6$ radical where $R^5$ and $R^6$ are each independently H or straight-chain or branched $C_1$-$C_7$-alkyl. In particular, $R^4$ is methyl, ethyl, n-propyl, isopropyl, n-butyl or isobutyl. Especially preferably, $R^4$ is methyl.

Useful alkali metal or alkaline earth metal hydroxides or carbonates are, for example, LiOH, NaOH, KOH, $LiCO_3$, $Na_2CO_3$, $K_2CO_3$. Preference is given to using alkali metal hydroxides such as sodium and potassium hydroxide which are preferably used in the form of aqueous solutions. For example, 1 to 50% by weight aqueous alkali metal hydroxide solutions may be used. Preference is given to 5 to 35% by weight solutions, particular preference to 10 to 25% by weight solutions. The alkali metal or alkaline earth metal hydroxides or carbonates can be used, for example, in amounts of 80 to 120 mol % based on haloformic esters used. This amount is preferably in the range of 90 to 110 mol %, more preferably in the range of 95 to 105 mol %.

Useful water-immiscible organic solvents are, for example, aliphatic and aromatic hydrocarbons, halogenated hydrocarbons, water-immiscible ethers or esters, and dialkyl carbonates. Preference is given to cyclohexane, toluene, xylene, methylene chloride and diethyl ether, in particular toluene and methylene chloride.

The water-immiscible organic solvent can be used, for example, in amounts of 20 to 90% by weight, preferably of 30 to 80% by weight, more preferably of 40 to 70% by weight, based on the haloformic ester of the formula (I).

The catalyst of the formula (I) is used generally, based on haloformic ester, in an amount of 0.001 to 0.5 mol %, preferably of 0.005 to 0.05 mol %.

The process according to the invention may be carried out in a pressure range of 1 to 10 bar, preferably of 1 to 1.5 bar.

The reaction temperature may, for example, lie between −10° C. and the boiling point (at standard pressure) of the haloformic ester used. It is preferably in the 0 to 50° C. range.

It is advantageous to ensure good mixing while carrying out the process according to the invention, for example by using stirrers, baffles or circulation pumps.

The process according to the invention may be carried out either batchwise or continuously. In batchwise mode, the reaction is preferably carried out in a stirred tank. In this case, depending on the size of the batch and the cooling performance present, the reaction is generally complete after 10 minutes to 3 hours.

Preference is given to carrying out the process according to the invention continuously using a stirred tank, a stirred tank battery or a tubular reactor. In this case, the average residence time in the reactor is generally between 1 and 60 minutes, preferably between 6 and 45 minutes and more preferably between 10 and 20 minutes.

After the process according to the invention has been carried out, if appropriate after cooling, the reaction mixture separates into two phases. In addition to the solvent, the organic phase comprises the dialkyl dicarbonate prepared and in some cases small amounts of unconverted haloformic ester and the catalyst. The aqueous phase comprises the inorganic salts formed as well as water.

The reaction product can be obtained in high purity from the organic phase by multistage distillation. The catalyst may be removed as high boilers and used again as the catalyst in the process according to the invention, if appropriate after a purification (recycling).

It is a particular and surprising advantage of the process according to the invention that the catalyst virtually does not catalyse the decomposition of the dialkyl dicarbonates after the reaction and can therefore be removed by distillation, as a result of which the isolated yield of end product is higher in comparison to conventional processes.

EXAMPLES

Example 1

1.17 g of trilaurylamine were initially charged in a mixture of 50 ml of toluene and 25 ml of water, and 43.8 g of methyl chloroformate were added dropwise with stirring at an internal temperature of 5° C. Subsequently, a solution of 35.6 g of 45% sodium hydroxide solution in 96.5 ml of water was added dropwise within 30 minutes and the temperature was kept at 15° C. After the mixture had been stirred for 40 minutes, the phases were separated. 23.1 g of dimethyl dicarbonate (85% of theory) were present in the organic phase.

Example 2

A mixture of 290 g of 13.8% by weight aqueous sodium hydroxide solution was added dropwise within 35 minutes to a mixture of 138 g of isobutyl chloroformate, 138 g of toluene and 1.42 g of tri-isooctylamine. In the course of this, the reaction temperature was kept at 30° C. The mixture was stirred for a further 15 minutes and cooled, and the phases were subsequently separated. 98.5 g of diisobutyl dicarbonate (=90% of theory) were present in the organic phase.

Example 3

473 g of 12.1% sodium hydroxide solution were pumped within 45 minutes into a mixture of 1.15 g of triisooctylamine, 180 ml of toluene and 156.9 g of methyl chloroformate, in such a way that it was possible to keep the temperature at approx. 17° C. with cooling. The mixture was stirred for a further 30 minutes and the phases were subsequently separated. 86.7 g of dimethyl dicarbonate (91% of theory) and 5.3 g of methyl chloroformate were present in the organic phase.

The present invention has been described with reference to specific details of particular embodiments and examples thereof. It is not intended that such details be regarded as limitations upon the scope of the invention except insofar as and to the extent that they are included in the accompanying claims.

What is claimed is:

1. A process for preparing dimethyl dicarbonates, comprising:

reacting methyl haloformates with at least one alkali metal hydroxide, alkaline earth metal hydroxide and/or carbonate in the presence of at least one water-immiscible organic solvent and in the presence of a catalyst, wherein the catalyst is at least one tertiary alkylamine of the formula (I)

$$NR^1R^2R^3 \quad (I)$$

where $R^1$, $R^2$ and $R^3$ are each independently straight-chain or branched $C_6$-$C_{25}$-alkyl.

2. The process according to claim 1, characterized in that the catalyst used is at least one tertiary alkylamine of the formula (I) according to claim 1 where $R^1$, $R^2$ and $R^3$ are each independently straight-chain or branched $C_8$-$C_{16}$-alkyl.

3. The process according to claim 1, characterized in that the catalyst used is at least one amine from the group of trisoctylamine, trisisooctylamine, trislaurylamine, and triscaprylylamine.

4. The process according to claim 1, characterized in that dimethyl dicarbonates of the formula (II)

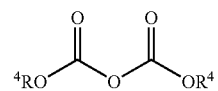

(II)

where $R^4$ is a methyl group are prepared by reacting methyl haloformates of the formula (III)

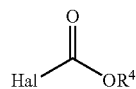

(III)

where

Hal is halogen and $R^4$ is as defined above.

5. The process according to claim 1, characterized in that the alkali metal hydroxides, alkaline earth metal hydroxides and/or carbonates are used in the form of aqueous solutions.

6. The process according to claim 1, characterized in that at least one water-immiscible organic solvent from the group of the aliphatic and aromatic hydrocarbons, the chlorinated hydrocarbons, the dialkyl carbonates or the water-immiscible ethers and esters is used.

7. The process according to claim 1, characterized in that the amount of tertiary trialkylamine of the formula (I) used is 0.001 to 0.5 mol % based on the methyl haloformates.

8. The process according to claim 1, characterized in that the reaction is carried out at a temperature between −10° C. and a boiling point (at standard pressure) of the methyl haloformates used.

9. The process according to claim 1, characterized in that the reaction is carried out in continuous mode.

10. The process according to claim 1, characterized in that, on completion of the reaction, the reaction mixture is worked up to remove the dimethyl carbonate by phase separation and subsequent multistage distillation of the organic phase.

11. The process according to claim 1, wherein $R^1$, $R^2$ and $R^3$ of the at least one tertiary alkylamine of the formula (I)

$$NR^1R^2R^3 \qquad (I)$$

are each independently straight-chain or branched $C_8$-alkyls.

12. A process for preparing dimethyl dicarbonates by reacting the corresponding methyl haloformates with at least one carbonate in the presence of at least one water-immiscible organic solvent and in the presence of a catalyst, wherein the catalyst is at least one tertiary alkylamine of the formula (I)

$$NR^1R^2R^3 \qquad (I)$$

and wherein $R^1$, $R^2$ and $R^3$ are each independently straight-chain or branched $C_6$-$C_{25}$-alkyl or $C_5$-$C_8$-cycloalkyl.

* * * * *